US00RE33791E

United States Patent [19]

Carr

[11] E

[45] Reissued

Patent Number: Re. 33,791

Date of Patent: Jan. 7, 1992

[54] NON-INVASIVE TEMPERATURE MONITOR

[75] Inventor: Kenneth L. Carr, Harvard, Mass.

[73] Assignee: M/A-COM, Inc., Burlington, Mass.

[21] Appl. No.: 455,289

[22] Filed: Dec. 22, 1989

Related U.S. Patent Documents

Reissue of:

[64] Patent No.: 4,715,727
Issued: Dec. 29, 1987
Appl. No.: 627,761
Filed: Jul. 5, 1984

[51] Int. Cl.[5] ..... A61N 5/02; G01J 5/00

[52] U.S. Cl. ..... 374/122; 128/736; 128/804; 219/10.55 H; 324/636

[58] Field of Search ..... 374/121, 122, 130; 219/10.55 A; 128/804, 736; 604/113, 114; 324/636

[56] References Cited

U.S. PATENT DOCUMENTS

| | | | |
|---|---|---|---|
| 3,742,394 | 6/1973 | Van Koughnett et al. | 324/640 X |
| 3,927,369 | 12/1975 | Billeter et al. | 374/117 X |
| 4,157,723 | 6/1979 | Granzow et al. | 604/905 X |
| 4,180,722 | 12/1979 | Clewans | 604/114 |
| 4,204,549 | 5/1980 | Paglione | 374/122 |
| 4,223,226 | 9/1980 | Quick et al. | 374/130 |
| 4,245,507 | 1/1981 | Samulski | 374/122 |
| 4,275,741 | 6/1981 | Edrich | 374/122 |
| 4,421,968 | 12/1983 | Osepchuk | 343/700 MS X |
| 4,471,192 | 9/1984 | Awata et al. | 219/10.55 A |
| 4,473,369 | 9/1984 | Lueders et al. | 604/113 X |
| 4,475,800 | 10/1984 | Popovich et al. | 604/29 |
| 4,479,127 | 10/1984 | Barbano | 219/10.55 F X |
| 4,532,939 | 8/1985 | Yuke | 374/122 X |
| 4,568,199 | 2/1986 | Schmidt | 374/122 |
| 4,614,514 | 9/1986 | Carr et al. | 604/113 |
| 4,622,447 | 11/1986 | Inoue | 219/10.55 A |
| 4,820,970 | 4/1989 | Swanson | 324/640 |

*Primary Examiner*—Daniel M. Yasich
*Attorney, Agent, or Firm*—Wolf, Greenfield & Sacks

[57] ABSTRACT

A non-invasive temperature monitoring apparatus used in association with a guided wave member that may be for the purpose of sterilization and that is adapted for microwave heating of a substance that is absorptive at microwave frequencies and that is held in some type of container or connector that is transparent at microwave frequencies. The apparatus comprises a length of waveguide. A coupling aperture is defined in the guided wave member. The length of waveguide is supported with one end thereof about the coupling aperture. A microwave radiometer detection circuit is also coupled from the length of waveguide for detecting on a continuing basis the temperature of the substance which is usually liquid being heated by the microwave energy.

30 Claims, 3 Drawing Sheets

NON-INVASIVE TEMPERATURE MONITOR

Matter enclosed in heavy brackets [ ] appears in the original patent but forms no part of this reissue specification; matter printed in italics indicates the additions made by reissue.

BACKGROUND OF THE INVENTION

The present invention relates in general to a non-invasive technique for monitoring the temperature of a material or substance that is absorptive at microwave frequencies while being held in a container, connector, bar, or the like that is transparent at microwave frequencies. More particularly, the non-invasive temperature monitor of the invention may be used in association with a microwave sterilizer for providing an accurate reading of the temperature of the material or substance being heated which in the case of microwave sterilization is typically a liquid, such as might be used in continuous ambulatory peritoneal dialysis (CAPD) microwave sterilization. Even more particularly, and in accordance with at least one embodiment of the present invention, there is provided a non-invasive technique for temperature measurement in a microwave sterilization apparatus and in which the liquid being sterilized is held within a connector means to be heated therein by microwave energy for the purpose of sterilization.

Reference is now made herein to copending application Ser. No. 466,894 filed Feb. 17, 1983, now U.S. Pat. No. 4,614,514, on a microwave sterilizer and assigned to the present assignee herein. This sterilizer is described therein as being used for the purpose of sterilizing a coupling or connector that intercouples a conduit from a source of liquid such as a saline solution to a conduit implanted in the body. The apparatus of this sterilizer comprises a guided wave member adapted to enclose the coupling or connector and means for heating by excitation of the guided wave member to heat an initial charge of the liquid to an elevated temperature for a time long enough to destroy bacteria. In this apparatus, it has been assumed that the proper sterilization occurs by virtue of the microwave power having been applied for a specified period of time. The basic problem that has come about is that, because the actual temperature of the liquid or solution is not being measured, one cannot be assured that sufficient sterilization has taken place. For example, if the microwave source is not functioning properly and is say, not putting out the require power, then even though the sterilization occurs for what appears to be a sufficient period of time, in fact, sufficient sterilization may not have occurred.

The common technique for measuring temperature is to monitor the surface of the container. However, if the container, connector, bar or the like is of insulating or semi-insulating material, it will not be possible to obtain exact temperature measurements. Also, there will tend to be a thermal lag.

Accordingly, it is an object of the present invention to provide a technique for monitoring the temperature, on a non-invasive basis, of a material or substance, usually a liquid, that is absorptive at microwave frequencies (also being heated by microwave energy) while being held in a container, bag, connector, or the like that is transparent at microwave frequencies.

Another object of the present invention is to provide a non-invasive technique for the measurement of temperature of a sterilizing substance which is usually a liquid in association with microwave heating of the liquid for sterilization purposes. In accordance with the invention, this combination of sterilization and temperature detection occurs without any interference whereby the heating applied is at a different frequency than the detection frequency.

Another object of the present invention is to provide a non-invasive temperature monitor that is of relatively simple construction, adapts itself readily to the microwave sterilizer and which can be made in miniature size and in which monitoring can occur quite easily so that the required temperature for sterilization can be readily achieved.

Still another object of the present invention is to provide an improved means for in particular, the warming of the solutions which are absorptive to microwave energy and which are typically contained in plastic bags or the like that are transparent to microwave energy.

A further object of the present invention is to provide a means as set forth in the preceding claim and which is in the form of a conformal array of elements particularly adapted for heating of relatively large solution bags or containers.

SUMMARY OF THE INVENTION

To accomplish the foregoing and other objects, features and advantages of the invention, there is provided a non-invasive temperature monitoring apparatus which is used in association with a guided wave means that may comprise part of a microwave sterilizer. This guided wave means is adapted for microwave heating of a substance of material, usually a liquid, that is absorptive at microwave frequencies and that is held in means, such as a container, bag, connector or the like, that is transparent to microwave energy. The apparatus of the present invention comprises a length of waveguide and means defining a coupling aperture in the guided wave means. The length of waveguide is supported with one end thereof about the coupling aperture for coupling energy from inside of the guided wave means to an opposite end of the length of waveguide. There is also provided a microwave radiometer detection circuit and means are provided for coupling from the length of waveguide to this detection circuit. The output of the detection circuit provides an accurate, high resolution temperature display output indicating on a continuous basis the temperature that is being detected of the material or substance (usually a liquid) that is being heated. The microwave heating is at one frequency and the detection is at a higher frequency. For example, the heating may be at 915 MHz while the detection may be designed at a frequency of 4.7 GHz. The coupling aperture preferably has a cross-sectional area less than the waveguide cross-sectional area. Also, the coupling aperture is dimensioned in comparison with the guided wave means so as to leave the heating characteristics of the guided wave means substantially undisturbed. Also, the waveguide is dimensioned to operate as a high pass filter passing the higher frequency and rejecting the lower heating frequency. The waveguide is simply designed so as to provide rejection by cut off of the lower frequency heating energy.

In accordance with another embodiment of the present invention, there is provided a non-invasive temperature monitoring apparatus used in association with a guided wave means in which this guided wave means is of generally larger size so as to accommodate a bag or container. In this embodiment of the invention, the microwave energy is used for the purpose of the warming of solutions absorptive to microwave energy contained in the plastic bag or container. The bag or container is transparent to microwave energy. In still another embodiment in accordance with the present invention there is provided an array of elements that are used in association with relatively large volume bags or containers. The array of elements may be disposed directly on the bag or container outer surface and the array enables heating and warming of materials or solutions contained in the bag. The array of elements provides good heat uniformity and the arrangement is particularly advantageous in connection with materials or solutions that are not good conductors of heat or that are not homogeneous.

BRIEF DESCRIPTION OF THE DRAWINGS

Numerous other objects, features and advantages of the invention should now become apparent upon a reading of the following detailed description taken in conjunction with the accompanying drawing, in which.

DETAILED DESCRIPTION

Figure 1:
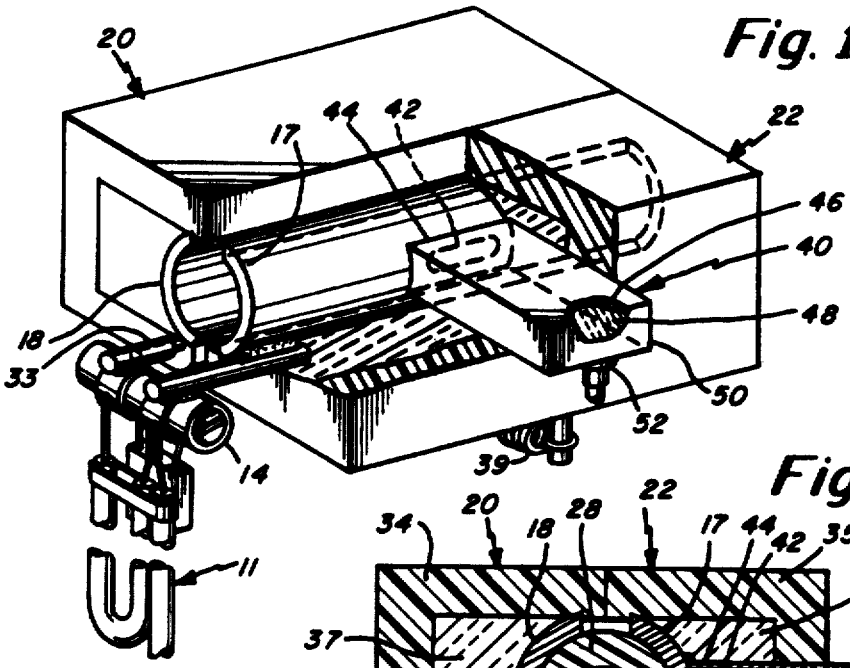
FIG. 1 is a perspective view illustrating the non-invasive temperature monitoring apparatus of the present invention as used in conjunction with a microwave sterilizer.
Figure 2:
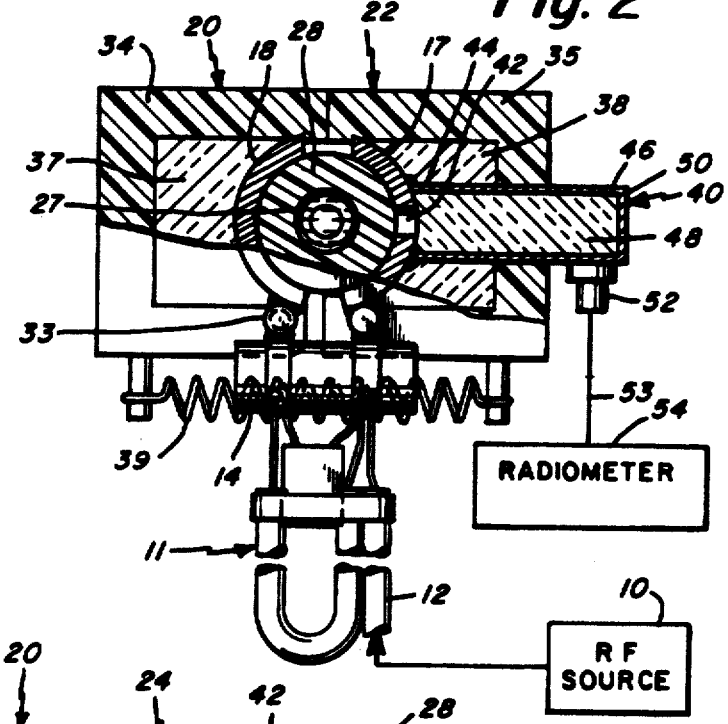
FIG. 2 is a cross-sectional view taken through the microwave sterilizer apparatus and the temperature monitoring apparatus.
Figure 3:
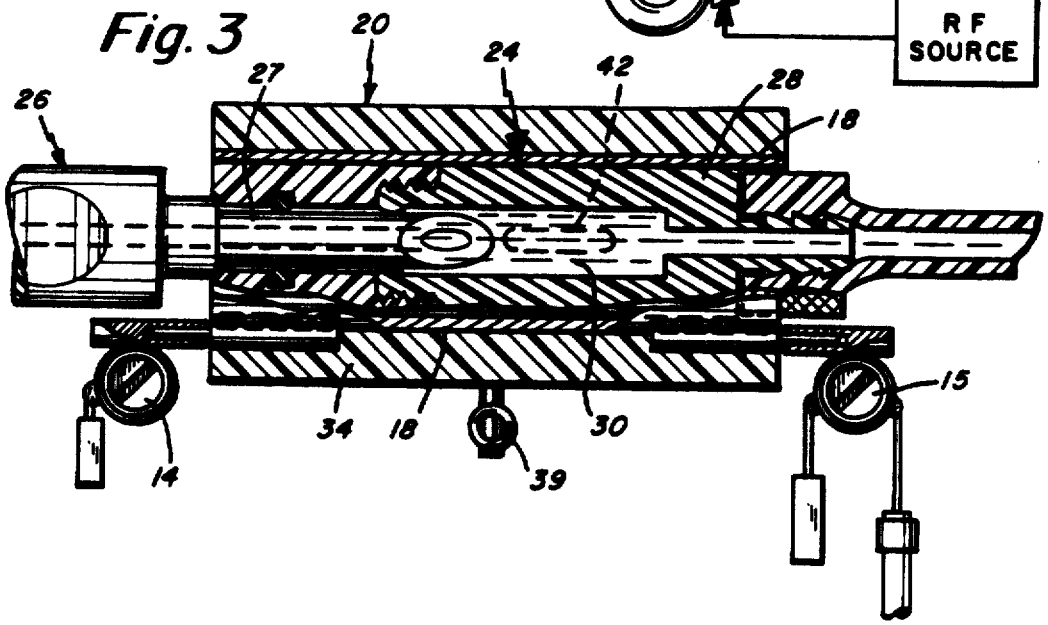
FIG. 3 is a longitudinal cross-sectional view additionally showing the connector means with a liquid being heated therein.

In FIGS. 1-3 herein, there is shown a technique for non-invasively monitoring the temperature of a liquid that is being heated by microwave energy for the purpose of sterilization. Thus, there is described herein at least part of a CAPD microwave sterilizer such as referred to in copending application Ser. No. 466,894 filed Feb. 16, 1983, now U.S. Pat. No. 4,614,514. Although the concepts of the invention are described primarily in connection with a CAPD microwave sterilizer, it is to be noted that the principles may also be applied to any device in which a material or substance that is absorptive at microwave frequencies is heated while being held in a container, bag, connector or the like that is transparent at microwave frequencies.

Reference may now be made to FIGS. 1-3 which shows a microwave sterilizer which is operated from a microwave source 10 which couples to a short coaxial cable 12. As noted in FIG. 2, there is also provided a balun 11 for converting from an unbalanced to a balanced configuration. Also depicted in FIG. 2, are the end tuning variable capacitors 14 and 15 for providing proper tuning of the guided wave structure. The electrical coupling is from capacitors 14 and 15 to conductors 17 and 18, respectively. The conductors 17 and 18 form a balanced transmission line which may be terminated in either a short circuit or open circuit. In this way the transmitter power not absorbed by the liquid initially is reflected, or directed back, into the lossy liquid. The loss of the structure is adequate to present a proper match to the microwave transmitter.

The microwave source 10 is preferably at a frequency of 950 MHz and operates from a typical voltage supply of say 12 volts, allowing safe operation from either battery or a low voltage power supply. The output of the 915 MHz solid state source is approximately 15 watts. With this low power operation, the device is thus compact, efficient, and safe in operation.

FIGS. 2 and 3 show the pivotal heater block 20 and the stationary heater block 22. The mechanical motions that are involved provide for the closing of the pivotal heater block 20 against the stationary heater block 22 enclosing the connector 24 which is comprised of the male member 26 and the female member 28. FIG. 2 shows the spike 27 of the male member 26 engaged with the female member 28. FIG. 3 also shows the liquid 30 that is being heated within the connector 24 for the purpose of sterilizing the connector 24.

As noted in FIG. 2, the two wire transmission line is comprised of the curved conductors 17 and 18. Each of these may be made of stainless steel to minimize heat transfer from the liquid. A rotary hinge joint 33 is provided to permit the pivotal movement of the heater block 20. Each of the heater blocks preferably also includes respective housing members 34 and 35 and internal insulation 37 and 38. The outer members 34 and 35 may be of plastic material and the insulation is adapted to maintain the heat concentrated within the connector 24.

FIGS. 2 and 3 also show the spring 39. This is disposed at the bottom of the heater blocks. This is instrumental in providing for an opening mechanism to the rotatable heater block 20. In FIG. 2 the end of the male spike 27 is shown inside of the female connector with the liquid thereabout in readiness for heating.

Now, in accordance with the present invention and in order to carry out the temperature monitoring on a non-invasive basis, there is provided a length of waveguide 40 that couples to one of the curved conductors comprising the guided wave member used for sterilization purposes. One of the curved conductors 17 is mechanically fixed in position and the fixed conductor preferably contains or incorporates the temperature sensor. In the illustration of FIGS. 1 and 2, the waveguide 40 couples from the curve member 17. This coupling of microwave energy to the waveguide 40 for temperature sensing is carried out by means of a coupling aperture 42 through the wall of the conductor 17. The waveguide 40 has its end 44 suitably secured to the curved conductor 17. This securing may be provided by means of a small weld or by some other suitable means of attachment. The coupling aperture is preferably uniformly centered relative to the waveguide 40. The coupling aperture is sufficiently small so as not to disturb the heating characteristics of the curved conductors 17 and 18. With regard to the length of the waveguide 40, this should be sufficiently long so as to provide a cut off at the lower frequency of 915 KHz. In this way the waveguide 40 functions as a high pass filter preventing any heating energy from being detected at the radiometer so that the radiometer detects only energy associated with the temperature of the liquid being sterilized.

The waveguide 40 is a dielectric filled waveguide. The waveguide thus includes a core of a ceramic material such as aluminum oxide with the outer boundaries of the waveguide being formed by means of a metallic conductive plating on the ceramic. This arrangement is depicted in FIG. 1 by a small cut out portion showing the plating and the ceramic material. In this regard, also note in FIG. 2, the plating 46 and the aluminum oxide core 48.

FIG. 2 also illustrates the coupling from the end 50 of the waveguide 40. This includes a connector 52 which is of conventional design coupling by way of line 53 to radiometer 54.

As indicated previously, in the preferred embodiment of the present invention, the waveguide 40 is dielectrically filled. The waveguide is constructed so as to provide adequate attenuation at the 915 MHz to prevent direct coupling of the heating frequency to the sensitive receiver.

In the example given in conjunction with a microwave sterilizer, it is noted that the plastic used in the connector 24 is low loss and therefore the radiometer reads primarily only the emission from the liquid contained therein. Also, the other curved conductor 18 such as depicted in FIGS. 1 and 2 functions as a reflector to direct energy back toward the coupling aperture which is also desired. This arrangement provides for good signal strength allowing the use of a relatively simple radiometer scheme.

Figure 4:
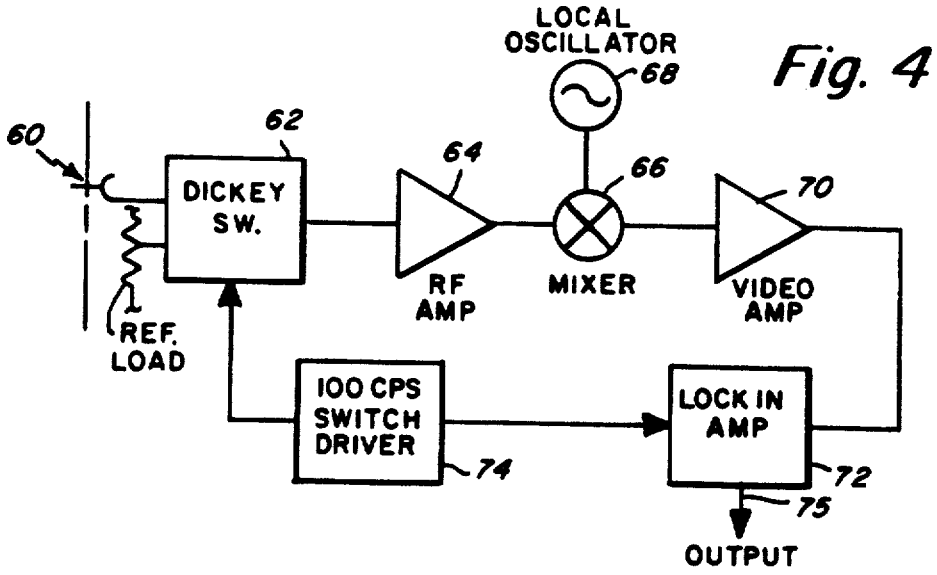
FIG. 4 is a circuit diagram of a microwave radiometer used for providing an indication of temperature being sensed.

FIG. 4 depicts the microwave radiometer circuit illustrating the waveguide coupling device at 60. This is representative of the waveguide 40 depicted in FIG. 2. The coupling device connects to the Dicke switch 62. The radiometer is preferably of the Dicke switch type utilizing a diode switch rather than a ferrite switch. This allows the use of a low cost microwave integrated circuit technique for fabrication of the circuit. In one version, the diode associated with the Dicke switch 62 may be supported across the waveguide 40. As indicated previously, the waveguide itself is sufficiently long enough to provide a cut off at the lower frequency of 915 MHz.

The output of the Dicke switch 62 couples to the RF amplifier 64. The output of the RF amplifier 64 couples to a mixer circuit 66 which also receives an output from the local oscillator 68. The output of the mixer 66 couples by way of the video amplifier 70 to the lock-in amplifier 72. There is also provided a low frequency 100 cycle per second switch driver 74 which is connected in a feedback arrangement for providing control to both the lock-in amplifier 72 and the Dicke switch 62. The output of the microwave radiometer circuit is taken at the output line 75 from the lock-in amplifier 72. For the most part the microwave radiometer circuit depicted in FIG. 4 is of conventional design and thus is not discussed in detail herein. The operation of this circuit is in substance the same as the operation of the circuit depicted in U.S. Pat. No. 4,346,716 also owned by the present assignee herein.

Figure 5:
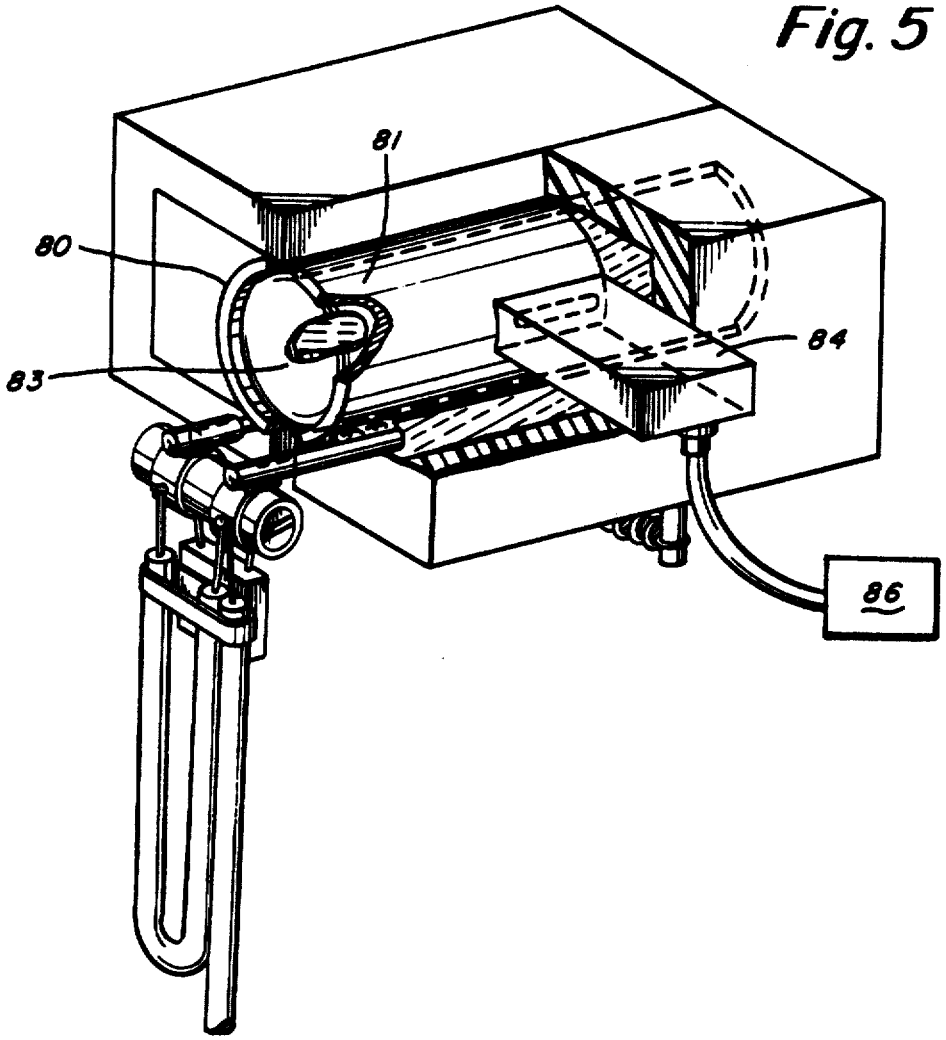
FIG. 5 is an alternate perspective view showing the non-invasive temperature monitoring apparatus of the present invention as used in association with a bag-type container for a liquid being heated.

FIG. 5 is a schematic diagram illustrating guided wave conductors 80 and 81 which may be of larger diameter than the conductors 17 and 18 illustrated in FIG. 1. The purpose of the embodiment to FIG. 5 is to illustrate the concepts of the invention in association with a bag 83 or the like container for containing a material which is usually a substance which is absorptive at microwave frequencies and which is being heated within the conductors 80 and 81 while being held in the container or bag with the container or bag being transparent at microwave frequencies. In the embodiment of FIG. 5, it is noted that there is also shown the waveguide 84 similar to the waveguide 40 of FIG. 2 and the coupling to a radiometer 86. The construction of the waveguide section 84 and the use of a coupling aperture in the conductor 81 may be substantially identical to that previously shown and described in connection with FIGS. 1–3.

The array of elements may be disposed directly on the bag or container outer surface and the array enables heating and warming of materials or solutions contained in the bag. The array of elements provides good heat uniformity and the arrangement is particularly advantageous in connection with materials or solutions that are not good conductors of heat or that are not homogeneous.

Figure 6:
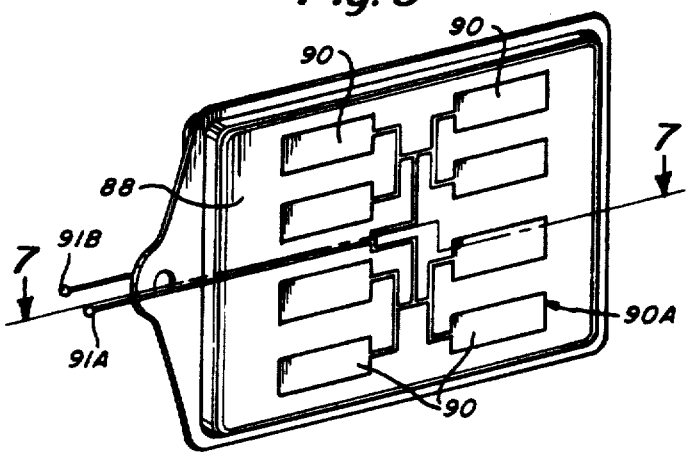
FIG. 6 is a perspective view showing a conformal array of elements that is used in connection with a bag or container for the purpose of heating or warming solutions contained in the bag or container.
Figure 7:
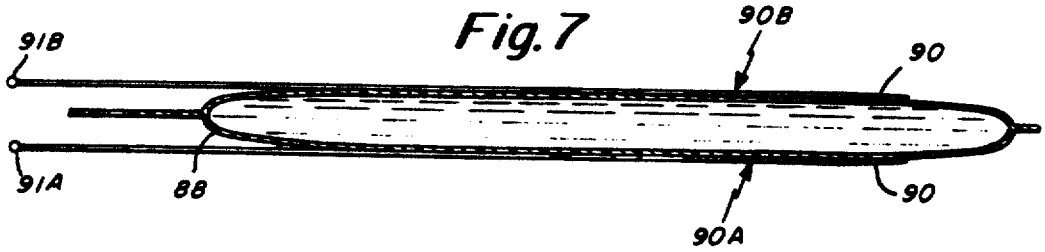
FIG. 7 is a cross-sectional view taken along the line 7—7 of FIG. 6 showing the matching array elements.

FIGS. 6 and 7 show the principles of the present invention as applied in connection with the heating or warming of a solution contained in a bag or container. Typically, this may be a two liter bag such as the bag 88 illustrated in FIG. 6. The bag 88 may contain a dialysate solution.

A conformal array of antenna elements 90 are disposed preferably one array on each side of the bag. In this connection, FIG. 7 shows element 90A on one side and element 90B on the opposite side. FIG. 7 also shows the corresponding terminals 91A and 91B. Each of the elements 90 is connected in common to one of the terminals as also illustrated in FIG. 6. The elements 90 may be deposited on the outer surface of the bag. The elements may be refracted onto the bag surface. The array of elements 90 is preferably disposed in a manner so as to cover the majority of the surface of the container. The elements 90 are also preferably disposed in some type of an orderly array so as to provide proper coverage and thus proper uniform heating.

Unlike microwave ovens used for heating, the array shown in FIGS. 6 and 7 provides for a much more uniform heating pattern. For example, in connection with a commercial microwave oven, because of the standing wave patterns established therein, there is a need for physically spinning or moving the material that is to be heated. The conventional microwave oven is far less efficient than the arrangement depicted in FIGS. 6 and 7 herein because in the microwave oven it is designed to heat a wide variety of materials of various sizes and shapes. On the other hand, in accordance with the present invention, the array is meant to heat only the solution contained within the bag.

Also, in accordance with the conformal array aspect of the invention depicted in FIGS. 6 and 7, much more flexibility is provided. For example, the array can be arranged so as to provide a non-uniform heating pattern if there would be some reason to heat one portion of the bag more than another portion. This might be the case where the bag is divided and contains two different types of liquids therein. One may desire to heat one of the liquids more than the other and in this connection the conformal array adapts itself very well to providing different heating patterns or even non-uniform heating patterns if desired.

It is also noted that all of the elements 90 of each group on each side of the bag is coupled out to a single terminal. This is illustrated in FIG. 7 as terminal 91A for elements on one side of the bag and terminal 91B coupling to elements on the opposite side of the bag. FIG. 6 also illustrates the electrical interconnections that essentially tie all of the elements 90 in common to terminal 91A in FIG. 6. Appropriate microwave energy is coupled to terminals 91A and 91B in the same manner as microwave energy is applied in connection with the embodiments described earlier.

Having now described a limited number of embodiments of the present invention, it should be apparent to those skilled in the art that numerous other embodiments may be contemplated as falling within the scope of this invention.

What is claimed is:

1. A temperature [appparatus] *apparatus* used in association with a guided wave means that is adapted for microwave heating, from a microwave heating source, of a substance that is absorptive at microwave frequencies and that is held in retaining means that is transparent at microwave frequencies, both said substance and said retaining means therefor being enclosed by said guided wave means, said apparatus comprising; a length of waveguide, means defining a coupling aperture in said guided wave means, means supporting said length of waveguide with one end thereof about said coupling aperture, a microwave radiometer detection circuit, means coupling from the length of waveguide to the detection circuit, wherein said microwave heating is at one frequency and the detection is at another frequency, and wherein said microwave heating and said microwave detection are at different frequencies, said coupling aperture having a cross-sectional area less than the waveguide cross-sectional area, the coupling aperture being sufficiently small in comparison to the waveguide cross-section so as to leave the heating characteristics of the [guides] *guided* wave means substantially undisturbed.

2. A non-invasive temperature monitoring apparatus as set forth in claim 1 wherein said length of the waveguide is sufficiently long so as to provide a cut-off at the heating frequency.

3. A non-invasive temperature monitoring apparatus as set forth in claim 1 wherein the length of the waveguide functions as a high pass filter preventing any heating energy from being detected at the radiometer detection circuits whereby the circuit detects only energy associated with the temperature of the liquid being heated.

4. A temperature monitoring *apparatus* used in association with a guided wave means that is adapted for microwave heating, from a microwave heating source, of a substance that is absorptive at microwave frequencies and that is held in retaining means that is transparent at microwave frequencies, both said substance and said retaining means therefor being enclosed by said guided wave means, said apparatus comprising; a length of waveguide, means [to] defining a coupling aperture in said guided wave means, means supporting said length of waveguide with one end thereof about said coupling aperture, a microwave radiometer detection circuit, means coupling from the length of waveguide to the detection circuit, and wherein said guided wave means comprises a pair of curved conductors, one having said coupling aperture therein and the other forming a reflector directing energy back to the coupling aperture to [provie] *provide* an enhanced signal thereat.

5. A temperature monitoring apparatus used in association with a guided wave means that is adapted for microwave heating, from a microwave heating source, of a substance that is absorptive at microwave frequencies and that is held in retaining means that is transparent at microwave frequencies, both said substance and said retaining means therefor being enclosed by said guided wave means, said apparatus comprising; a length of waveguide, means defining a coupling aperture in said guided wave means, means supporting said length of waveguide with one end thereof about said coupling aperture, a microwave radiometer detection circuit, means coupling from the length of waveguide to the detection circuit, wherein said microwave heating is at one frequency and the detection is at another frequency, and wherein the coupling aperture is dimensioned in comparison to the guided wave means so as to leave the heating characteristics of the guided wave means substantially undisturbed.

6. A temperature monitoring apparatus used in association with a guided wave means that is adapted for microwave heating, from a microwave heating source, of a substance that is absorptive at microwave frequencies and that is held in retaining means that is transparent at microwave frequencies, both said substance and said retaining means therefor being enclosed by said guided wave means, said apparatus comprising; a length of waveguide, means [to] defining a coupling aperture in said guided wave means, means supporting said length of waveguide with one end thereof about said coupling aperture, a microwave radiometer detection circuit, means coupling from the length of waveguide to the detection circuit, wherein said microwave heating is at one frequency and the detection is at another frequency, and wherein the length of waveguide is selected so that the waveguide operates as a filter passing said detection frequency and rejecting said heating frequency.

7. A temperature monitoring apparatus in combination with a guided wave means used for sterilization and/or heating of a substance, comprising means for operating the guided wave means to provide microwave heating of the substance in a container, said substance being absorptive at microwave frequencies and wherein said container is transparent in microwave frequencies, both said substance and said container being enclosed by said guided wave means, a length of waveguide, means defining a coupling aperture in said guided wave means, means supporting said length of waveguide with one end thereof about said coupling aperture, a microwave radiometer detection circuit and signal coupling means coupling from the length of waveguide, at a location remote from said coupling aperture, to the detection circuit.

8. A non-invasive temperature monitoring apparatus as set forth in claim 7 wherein said waveguide is dielectric filled.

9. A non-invasive temperature monitoring apparatus as set forth in claim 7 wherein said microwave heating is at one frequency and the detection is at a higher frequency, said coupling aperture having a cross-sectional area less than the waveguide cross-sectional area, the coupling aperture being smaller in comparison with the guided wave means so as to leave the heating characteristics of the guided wave means substantially undisturbed, said waveguide being dimensioned to operate as a high pass filter passing said higher frequency and rejecting said heating frequency.

10. A non-invasive temperature monitoring apparatus as set forth in claim 7 wherein said substance that is absorptive at microwave frequencies comprises a liquid and said container comprises a coupling means.

11. A non-invasive temperature monitoring apparatus as set forth in claim 7 wherein said substance that is absorptive at microwave frequencies comprises a liquid and said container comprises a connector means.

12. A non-invasive temperature monitoring apparatus as set forth in claim 7 wherein said substance that is absorptive at microwave frequencies comprises a liquid.

*13. A temperature monitoring apparatus used in association with a guided wave means that is adapted for microwave heating, from a microwave heating source, of a substance that is absorptive at microwave frequencies and that is located during temperature monitoring in means transparent at microwave frequencies, both said substance and said transparent means being surrounded by said guided wave means, said apparatus comprising; electromagnetic transmission means adapted for the transmission of microwave energy at selected frequencies, means defining a coupling aperture in said guided wave means, means supporting said electromagnetic transmission means with one end thereof about said coupling aperture, a microwave radiometer detection circuit, and, means coupling said electromagnetic transmission means to the detection circuit, wherein microwave heating is at one frequency and detection is at another frequency, and wherein said microwave heating and said microwave detection are at different frequencies, said coupling aperture having a cross-sectional area less than electromagnetic transmission means cross-sectional area, the coupling aperture being sufficiently small in comparison to said electromagnetic transmission means cross-section so as to leave the heating characteristics of the guided wave means substantially undisturbed.*

*14. A non-invasive temperature monitoring apparatus as set forth in claim 13 wherein said electromagnetic transmission means comprises a length of waveguide that is sufficiently long so as to provide a cut-off at the heating frequency.*

*15. A non-invasive temperature monitoring apparatus as set forth in claim 13 wherein said electromagnetic transmission means functions as a high pass filter preventing any heating energy from being detected at the radiometer detection circuits whereby the circuit detects only energy associated with the temperature of the liquid being heated.*

*16. A temperature monitoring apparatus used in association with a guided wave means that is adapted for microwave heating, from a microwave heating source, of a substance that is absorptive at microwave frequencies and that is located during temperature monitoring in means transparent at microwave frequencies, both said substance and said transparent means being surrounded by said guided wave means, said apparatus comprising; electromagnetic transmission means adapted for the transmission of microwave energy at selected frequencies, means defining a coupling aperture in said guided wave means, means supporting said electromagnetic transmission means with one end thereof about said coupling aperture, a microwave radiometer detection circuit, and, means coupling said electromagnetic transmission means to the detection circuit, wherein said guided wave means comprises a pair of curved conductors, one having said coupling aperture therein and the other forming a reflector directing energy back to the coupling aperture to provide an enhanced signal thereat.*

*17. A temperature monitoring apparatus used in association with a guided wave means that is adapted for microwave heating, from a microwave heating source, of a substance that is absorptive at microwave frequencies and that is located during temperature monitoring in means transparent at microwave frequencies, both said substance and said transparent means being surrounded by said guided wave means, said apparatus comprising; electromagnetic transmission means adapted for the transmission of microwave energy at selected frequencies, means defining a coupling aperture in said guided wave means, means supporting said electromagnetic transmission means with one end thereof about said coupling aperture, a microwave radiometer detection circuit for microwave detection, and, means coupling said electromagnetic transmission means to the detection circuit, wherein microwave heating from the microwave heating source is at one frequency and the microwave detection by said microwave radiometer detection circuit is at another frequency, and wherein the coupling aperture is dimensioned in comparison to the guided wave means so as to leave the heating characteristics of the guided wave means substantially undisturbed.*

*18. A temperature monitoring apparatus used in association with a guided wave means that is adapted for microwave heating, from a microwave heating source, of a substance that is absorptive at microwave frequencies and that is located during temperature monitoring in means transparent at microwave frequencies, both said substance and said transparent means being surrounded by said guided wave means, said apparatus comprising; electromagnetic transmission means adapted for the transmission of microwave energy at selected frequencies, means defining a coupling aperture in said guided wave means, means supporting said electromagnetic transmission means with one end thereof about said coupling aperture, a microwave radiometer detection circuit for microwave detection, and, means coupling said electromagnetic transmission means to the detection circuit, wherein microwave heating from the microwave heating source is at one frequency and the microwave detection by said microwave radiometer detection circuit is at another frequency, and wherein the electromagnetic transmission means is selected so that it operates as a filter passing a detection frequency and rejecting a heating frequency.*

*19. A temperature monitoring apparatus in combination with a guided wave means used for sterilization and/or heating of a substance, comprising means for operating the guided wave means to provide microwave heating of the substance in a container, said substance being absorptive at microwave frequencies and wherein said container is transparent in microwave frequencies, both said substance and said container being surrounded by said guided wave means, an electromagnetic transmission means, means defining a coupling aperture in said guided wave means, means supporting said electromagnetic transmission means with one end thereof disposed about said coupling aperture, a microwave radiometer detection circuit and signal coupling means coupling from said electromagnetic transmission means, at a location remote from said coupling aperture, to the detection circuit.*

*20. A non-invasive temperature monitoring apparatus as set forth in claim 19 wherein said electromagnetic transmission means is dielectric filled.*

*21. A non-invasive temperature monitoring apparatus as set forth in claim 19 wherein said microwave heating is at one frequency and the detection is at a higher frequency said coupling aperture having a cross-sectional area less than the electromagnetic transmission means cross-sectional area, the coupling aperture being smaller in comparison with the guided wave means so as to leave the heating characteristics of the guided wave means substantially undisturbed, said electromagnetic transmission means*

*being dimensioned to operate as a high pass filter passing said higher frequency and rejecting said heating frequency.*

*22. A non-invasive temperature monitoring apparatus as set forth in claim 19 wherein said substance that is absorptive at microwave frequencies comprises a liquid and said container comprises a coupling means.*

*23. A non-invasive temperature monitoring apparatus as set forth in claim 19 wherein said substance that is absorptive at microwave frequencies comprises a liquid and said container comprises a connector means.*

*24. A non-invasive temperature monitoring apparatus as set forth in claim 19 wherein said substance that is absorptive at microwave frequencies comprises a liquid.*

*25. A temperature monitoring apparatus used in association with a guided wave means that is adapted for microwave heating, from a microwave heating source, of a substance that is absorptive at microwave frequencies and is located during temperature monitoring in means transparent at microwave frequencies, both said substance and said transparent means being surrounded by said guided wave means, said apparatus comprising; electromagnetic transmission means adapted for the transmission of microwave energy at selected frequencies, means defining a coupling port in said guided wave means, means supporting said electromagnetic transmission means with one end thereof about said coupling port, a microwave radiometer detection circuit for microwave detection, and, means coupling said electromagnetic transmission means to the detection circuit, wherein microwave heating from the microwave heating source is at one frequency and the microwave detection by said microwave radiometer detection circuit is at another frequency, and wherein the coupling part is dimensioned in comparison to the guided wave means so as to leave the heating characteristics of the guided wave means substantially undisturbed.*

*26. A non-invasive temperature monitoring apparatus as set forth in claim 24, wherein said liquid is stationary during said microwave heating.*

*27. A non-invasive temperature monitoring apparatus used in association with a guided wave means that is adapted for microwave heating of a substance that is absorptive at microwave frequencies and that is held in means that is transparent at microwave frequencies, said apparatus comprising; a length of waveguide, means defining a coupling aperture in said guided wave means, means supporting said length of waveguide with one end thereof about said coupling aperture, a microwave radiometer detection circuit, and means coupling from the length of waveguide to the detection circuit, wherein said microwave heating is at one frequency and the detection is at a higher frequency, and wherein said coupling aperture has a cross-sectional area less than the waveguide cross-sectional area.*

*28. A non-invasive temperature monitoring apparatus as set forth in claim 27 wherein the coupling aperture is dimensioned in comparison with the guide wave means so as to leave the heating characteristics of the guided wave means substantially undisturbed.*

*29. A non-invasive temperature monitoring apparatus as set forth in claim 28 wherein the waveguide is dimensioned to operate as a high pass filter passing said higher frequency and rejecting said one frequency.*

*30. A non-invasive temperature monitoring apparatus in combination with a guided wave means used for sterilization and including means for operating the guided wave means to provide microwave heating of a substance that is absorptive at microwave frequencies and that includes a container or the like for the substance which container is transparent at microwave frequencies, a length of waveguide, means defining a coupling aperture in said guided wave means, means supporting said length of waveguide with one end thereof about said coupling aperture, a microwave radiometer detection circuit and means coupling from the length of waveguide to the detection circuit, wherein said microwave heating is at one frequency and the detection is at a higher frequency, said coupling aperture having a cross-sectional area less than the waveguide cross-sectional area, the coupling aperture being dimensioned in comparison with the guided wave means so as to leave the heating characteristics of the guided wave means substantially undisturbed, said waveguide being dimensioned to operate as a high pass filter passing said higher frequency and rejecting said heating frequency.*

* * * * *